United States Patent
Kourai et al.

(10) Patent No.: US 6,251,381 B1
(45) Date of Patent: Jun. 26, 2001

(54) ANTIBACTERIAL AND ANTIFUNGAL RESIN COMPOSITION

(75) Inventors: Hiroki Kourai; Takuya Maeda, both of Tokushima; Munehiro Yoshida, Takamatsu; Kensei Kunikata, Kita-gun; Kouji Wada, Ayauta-gun, all of (JP)

(73) Assignee: Inui Corporation, Osaka (JP)

( * ) Notice: Subject to any disclaimer, the term of this patent is extended or adjusted under 35 U.S.C. 154(b) by 0 days.

(21) Appl. No.: 09/431,051

(22) Filed: Nov. 1, 1999

(30) Foreign Application Priority Data

Nov. 4, 1998 (JP) .................................... 10-313139
Dec. 28, 1998 (JP) .................................... 10-373741

(51) Int. Cl.⁷ ................................ A61L 9/00; A61L 9/01; A01N 25/34
(52) U.S. Cl. .......................................... 424/76.1; 424/404
(58) Field of Search ..................................... 424/404, 76.1

(56) References Cited

U.S. PATENT DOCUMENTS 3,786,058  1/1974  Edwards .......................... 260/294.8

FOREIGN PATENT DOCUMENTS

WO 9324003A  12/1993  (WO) .

OTHER PUBLICATIONS

Japanese Laid–open Publication 56–040587 (English abstract).
Japanese Laid–open Publication 7–149713 (English abstract).
Japanese Laid–open Publication 10–029969 (English abstract).
Japanese Laid–open Publication 10–297089 (English abstract).
Nagamune et al., "Evaluation of the cytotoxic effects of bis–quaternary ammonium antimicrobial reagents on human cells", Toxicology in Vitro, pp. 139–147, 2000.*
Database WPI, Section Ch, Week 199727, Derwent Publications Ltd., London GB & JP 09 110692 A (INUI KK), Apr. 28, 1997 (Abstract).
Database WPI, Section Ch, Week 199825, Derwent Publications Ltd., London GB & JP 10 095773 A (INUI KK, Apr. 14,1998 (Abstract).
Database WPI, Section Ch, Week 199902, Derwent Publications Ltd., London GB & JP 10 287566 A (INUI KK), Oct. 27, 1998 (Abstract).
Japanese Patent Laid–Open No. 259054/89, Published Oct. 16, 1989.
Japanese Patene Laid–Open No. 207090/95, Published Aug. 8, 1995.
Japanese Patent Laid–Open No. 324070/97, Published Dec. 16, 1997.
Japanese Patent Publication No. 17058/92, Published Dec. 2, 1992.
Japanese Patent Laid–Open No. 24594/94, Published Sep. 6, 1994.

* cited by examiner

Primary Examiner—Thurman K. Page
Assistant Examiner—S. Howard

(57) ABSTRACT

The present invention provides an antibacterial and antifungal resin composition comprising a polymeric resin and an antibacterial bis-pyridinium compound of the general formula

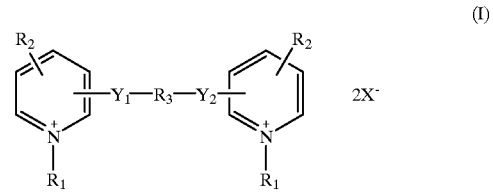

wherein the two $R_1$ may be the same or different, and each represent an alkyl group of 1 to 18 carbon atoms or an alkenyl group of 3 to 18 carbon atoms; the two $R_2$ may be the same or different, and each represent a hydrogen atom, a halogen atom, a hydroxyl group, an amino group, an alkyl group of 1 to 6 carbon atoms, or an alkoxy group of 1 to 3 carbon atoms; $R_3$ represents an alkylene group of 2 to 18 carbon atoms, an alkenylene group of 3 to 18 carbon atoms, or a phenylene or xylylene group which may optionally be substituted by an alkyl group of 1 to 18 carbon atoms, an alkoxy group of 1 to 6 carbon atoms, or an alkoxycarbonyl group of 2 to 6 carbon atoms; $Y_1$ represents —NHCO—, —CONH—, —NHCS—, —COO—, —COS—, —O— or —S—; $Y_2$ represents —CONH—, —NHCO—, —CSNH—, —OOC—, —SOC—, —O— or —S—; and X represents an anion.

10 Claims, No Drawings

ANTIBACTERIAL AND ANTIFUNGAL RESIN COMPOSITION

This invention relates to antibacterial and antifungal resin compositions which can be used in a wide range of applications requiring antibacterial and antifungal properties from the viewpoint of health and hygiene, such as various antimicrobial goods including wallpaper and sanitary products.

Moldings formed of polymeric resins essentially have relatively good antifungal properties, and are hence being used as surfacing materials for various building materials, household goods, insoles of shoes, and the like. In order to further improve their antifungal properties, it has been common practice to incorporate various antifungal agents, such as those of the arsenic, imidazole and thiazole types, in the polymeric resins (see, for example, Japanese Patent Laid-Open No. 259054/'89 and 207090/'95).

However, as a result of the recently diversified use of resin products, it has become insufficient to inhibit the growth of fungi alone, and moreover there is a growing demand for products also having sufficient resistance to various kinds of bacteria such as *Staphylococcus aureus* and *Escherichia coli*. For example, fibrous materials capable of inhibiting the growth of methicillin-resistant *Staphylococcus aureus* (MRSA) which is posing a serious problem with hospital infection. Moreover, domestic appliances (e.g., refrigerators, washing machines and dish dryers) using plastic components having incorporated therein antibacterials for inhibiting the propagation of *Escherichia coli* are being put to practical use.

Examples of antibacterials incorporated in polymeric resins include Quaternary ammonium salts and biguanides (see, for example, Japanese Patent Laid-Open No. 259054/'89 and 324070/'97). These antibacterials are effective against bacteria, but have no antifungal effect. In order to obtain polymeric resin products having antibacterial and antifungal properties, antifungal agents must be used in combination with them.

Meanwhile, in recent years, disposable diapers, whether for babies or for adults, are being increasingly used in place of cloth diapers, because of their excellent absorption capacity and convenience in handling. It is expected that, in future, demand for disposable diapers will continue to expand with the spread of their use. Generally, disposable diapers consist of a water-pervious facing sheet, a water-impervious backing sheet, and a water-absorbing layer interposed between these sheets. For the water-absorbing layer, there is used pulp, a highly water-absorbing polymer or the like.

Conventionally, three requirements concerning leakproofness of excretion, skin care and ease of use have been imposed on disposable diapers. Although all disposable diapers now appearing on the market meet these requirements almost satisfactorily, the existing state of the art is such that none of them have a sufficient deodorant function in eliminating the odor of urinary excretion. Generally, the odor of urinary excretion from babies is not very strong. However, adults, particularly those requiring diapers, are in a morbid state and are undergoing drug administration in many cases. Moreover, they are frequently in an unhygienic condition owing to inadequate care. For these reasons, their urinary excretion tends to emit an offensive odor. Accordingly, there is an increasing need for disposable diapers having excellent deodorant properties.

As to the cause for the generation of an offensive odor, it is believed that, by urea-hydrolyzing enzymes and other enzymes produced by skin flora bacteria and the like, urea and other compounds present in urine are decomposed to ammonia, methylamine and like compounds which are responsible for an offensive odor. Accordingly, in order to prevent an offensive odor arising from urinary excretion in the use of a disposable diaper, it is necessary to prevent the propagation of bacteria in the water-absorbing layer of the diaper. In order to solve this problem by adding antibacterials to the water-absorbing organic polymer, there have been proposed, for example, a method using Quaternary ammonium salts and/or biguanides (see Japanese Patent Publication No. 17058/'92) and a method using a Quaternary ammonium salt with silyl group (see Japanese Patent Laid-Open No. 245954/'94).

However, since these antibacterials are scarcely effective against bacteria producing an enzyme (urease) capable of degrading urea and other compounds present in urea to ammonia, methylamine and the like, a satisfactory deodorant effect is not always contributed.

An object of the present invention is to provide a resin composition which exhibits not only an excellent antibacterial effect on both gram-positive and gram-negative bacteria, but also an excellent antifungal effect, and can hence been used in a wide range of applications requiring antibacterial and antifungal properties from the viewpoint of health and hygiene.

Another specific object of the present invention is to provide a water-absorbing deodorant resin composition which exhibits an excellent antibacterial effect on bacteria producing substances responsible for an offensive odor from urea and other compounds present in urine, particularly skin flora bacteria capable of producing urease, also shows a broad antibacterial spectrum against gram-positive and gram-negative bacteria, and is markedly effective in preventing the generation of an offensive odor arising from urinary excretion.

Other objects and advantages of the present invention will become apparent from the following detailed description.

According to the present invention, there is provided an antibacterial and antifungal resin composition comprising a polymeric resin and antibacterial bis-pyridinium compound of the general formula

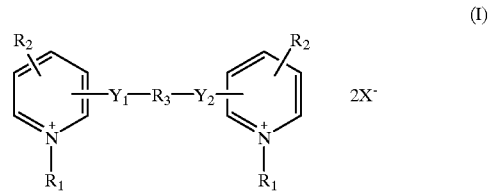

(I)

wherein the two $R_1$ may be the same or different, and each represent an alkyl group of 1 to 18 carbon atoms or an alkenyl group of 3 to 18 carbon atoms; the two $R_2$ may be the same or different, and each represent a hydrogen atom, a halogen atom, a hydroxyl group, an amino group, an alkyl group of 1 to 6 carbon atoms, or an alkoxy group of 1 to 3 carbon atoms; $R_3$ represents an alkylene group of 2 to 18 carbon atoms, an alkenylene group of 3 to 18 carbon atoms, or a phenylene or xylylene group which may optionally be substituted by an alkyl group of 1 to 18 carbon atoms, an alkoxy group of 1 to 6 carbon atoms, or an alkoxycarbonyl group of 2 to 6 carbon atoms; $Y_1$ represents —NHCO—, —CONH—, —NHCS—, —COO—, —COS—, —O— or —S—; $Y_2$ represents —CONH—, —NHCO—, —CSNH—, —OOC—, —SOC—, —O— or —S—; and X represents anions.

According to a specific embodiment of the present invention, there is provided a deodorant water-absorbing resin composition comprising a highly water-absorbing resin and antibacterial bis-pyridinium compound of the above general formula (I).

The antibacterial and antifungal resin compositions of the present invention will be more specifically described hereinbelow.

As used herein, the term "alkyl group" denotes a straight-chain or branched alkyl group, and examples thereof include methyl, ethyl, propyl, isopropyl, butyl, isobutyl, sec-butyl, pentyl, isopentyl, sec-pentyl, hexyl, heptyl, octyl, 2-ethylhexyl, nonyl, decyl, isodecyl, dodecyl, tetradecyl, hexadecyl and octadecyl, etc. From the viewpoint of antibacterial power, the alkyl groups represented by $R_1$ are preferably ones having 8 or more carbon atoms. The term "alkenyl group" denotes a straight-chain or branched alkenyl group, and examples thereof include allyl, methallyl, pentenyl, hexenyl, heptenyl, octenyl, nonenyl, decenyl, undecenyl, dodecenyl, tetradecenyl, hexadecenyl and octadecenyl, etc.

The term "alkoxy group" denotes an alkyloxy group in which the alkyl moiety has the above-described meaning, and examples thereof include methoxy, ethoxy, propoxy, isopropoxy, butoxy, isobutoxy, sec-butoxy and tert-butoxy.

The term "alkylene group" preferably denotes a group of the formula $—(—CH_2—)_n—$. In this formula, n is preferably in the range of 2 to 18 and more preferably 3 to 8.

The term "alkenylene group" comprehends, for example, —CH=CH—, —CH=CH—CH$_2$— and —CH$_2$—CH=CH—CH$_2$—.

The term "alkoxycarbonyl group" denotes an alkyloxycarbonyl group in which the alkyl moiety has the above-described meaning, and examples thereof include methoxycarbonyl and ethoxycarbonyl.

The term "halogen atom" comprehends fluorine, chlorine, bromine and iodine.

The term "anion" comprehends inorganic anions such as halogen ions (e.g., $Cl^-$, $Br^-$ and $I^-$) and nitrate ion ($NO_3^-$); and organic acid anions such as acetate ion ($CH_3COO^-$) and propionate ion ($C_2H_5COO^-$).

Among the compounds represented by the above formula (I), a preferred group of compounds are those of formula (I) in which the two $R_1$ may be the same or different, and each represent an alkyl group of 8 to 18 carbon atoms; the two $R_2$ may be the same or different, and each represent a hydrogen atom or a chlorine atom; $R_3$ represents an alkylene group of 3 to 8 carbon atoms, a phenylene group or a xylylene group; $Y_1$ represents —NHCO—, —CONH—, —COO— or —S—; $Y_2$ represents —CONH—, —NHCO—, —OOC— or —S—; and X represents a halogen ion or an acetate ion.

Specific examples of the compounds of the above formula (I) used as antibacterials in the present invention are as follows:

N,N'-Hexamethylenebis(4-carbamoyl-1-decylpyridinium bromide) ("Dimer 38"; manufactured by INUI CORPORATION), N,N'-hexamethylenebis(4-carbamoyl-1-decylpyridinium acetate) ("Dimer 38A"; manufactured by INUI CORPORATION), 4,4'-(tetramethylenedicarbonyldiamino)bis(1-decylpyridinium bromide) ("Dimer 136"; manufactured by INUI CORPORATION), 4,4'-(tetramethylenedicarbonyldiamino)bis(1-decylpyridinium acetate) ("Dimer 136A"; manufactured by INUI CORPORATION), 1,4-tetramethylenebis(4-carbamoyl-1-hexadecylpyridinium bromide), 1,6-hexamethylenebis(3-carbamoyl-1-dodecylpyridinium bromide), 1,6-octamethylenebis(3-carbamoyl-1-tetradecylpyridinium bromide), 3,3'-(1,3-trimethylenedicarbonyldiamino)bis(1-dodecylpyridinium bromide), 4,4'-(p-xylyldithio)bis(1-octylpyridinium iodide), 3,3'-(m-xylyldithio)bis(1-tetradecylpyridinium bromide), N,N'-(p-phenylene)bis(4-carbamoyl-1-octylpyridinium bromide), N,N'-(m-phenylene)bis(3-carbamoyl-1-dodecylpyridinium bromide), 4,4'-(p-phthalamido)bis(1-octylpyridinium bromide), 3,3'-(m-phthalamido)bis(1-octadecylpyridinium iodide), 4,4'-(1,8-octamethylenedioxy)bis(1-dodecylpyridinium bromide), 3,3'-(1,6-hexamethylenedioxy)bis(1-hexadecylpyridinium bromide), 4,4'-(1,6-hexamethylenedioxydicarbonyl)bis(1-octylpyridinium bromide), 3,3'-(1,6-tetramethylenedioxydicarbonyl)bis(1-dodecylpyridinium bromide), 4,4'-(1,4-tetramethylenedicarbonyldioxy)bis(1-octylpyridinium bromide), 3,3'-(p-phthaloyldioxy)bis(1-decylpyridinium chloride), 4,4'-(1,8-octamethylenedicarbonyldithioxy)bis(1-octadecylpyridinium bromide) and 3,3'-(m-phthaloyldithioxy)bis(1-decylpyridinium iodide).

The compounds of the above formula (I) are disclosed, for example, in the publications of Japanese Patent Laid-Open Nos. 110692/'97, 95773/'98 and 287566/'98 and the specifications of Japanese Patent Application Nos. 282071/'98 and 321347/'98, all of which were filed in the name of the present applicant, or may be prepared according to the processes described in these publications or specifications.

On the other hand, no particular limitation is placed on the type of the polymeric resin in which the antibacterial compound of the above formula (I) is incorporated according to the present invention, and any desired polymeric resin may be freely chosen according to the intended use of the resin composition of the present invention, and the like. Concrete examples of usable resins include vinyl chloride polymers, urethane polymers, acrylate polymers, olefin polymers, ethylene polymer, propylene polymer, polyamides, ethylene-vinyl acetate copolymers, vinylidene chloride polymer, styrene polymers, ester polymers, nylons, cellulose derivatives, polycarbonates, fluorinated resins, silicone resins, vinyl alcohol polymers, vinyl ester polymers, compounds and natural rubber. These resins may be used alone or as a blend of two or more.

The antibacterial and antifungal resin compositions of the present invention may be prepared by dispersing an antibacterial compound of the above formula (I) in a polymeric resin as described above. More specifically, the resin compositions of the present invention may be obtained, for example, by adding the compound of formula (I) in the polymeric resin and melt-kneading this mixture, by adding the compound of formula (I) or a solution thereof to a solution of the polymeric resin and agitating this mixture, or by polymerizing a monomer and monomers with the compound of formula (I) or a solution thereof Alternatively, the compound of formula (I) may be chemically bonded to the polymeric resin.

The amount of the compound of formula (I) incorporated in the polymeric resin is not strictly limited, but may vary according to the type of the resin used, the type of the compound of formula (I) used, the use of the resulting resin composition, and the like. However, the amount is generally in the range of 0.001 to 10 parts by weight, preferably 0.005 to 5 parts by weight, and more preferably 0.01 to 2 part by weight, per 100 parts by weight of the polymeric resin.

If necessary, plasticizers, fillers, colorants (i.e., dyes and pigments), ultraviolet-radiation absorbers and other additives may optionally be incorporated in the resin compositions of the present invention.

The resin compositions of the present invention may be processed into various forms according to their intended use and the like. For example, according to per se known resin processing techniques such as extrusion molding, injection molding, solution casting and spinning, the resin compositions of the present invention may be formed into films, sheets, plates, fibers or three-dimensional articles, and may be used, for concrete example, as interior decorative materials (e.g., wallpaper), as flooring materials (e.g., tiles), and in home electrical appliances (e.g., refrigerators, washing machines and dryers).

Moreover, the resin compositions of the present invention may also be formed into antibacterial paints by using them as vehicles. This can be done, for example, by dissolving or dispersing the resin composition in a paint solvent and adding suitable paint additives (e.g., pigments and crosslinking agents) to the resulting solution or dispersion.

Furthermore, in order to impart antibacterial and antifungal processing to fibrous or textile products and paper products, the resin compositions of the present invention may be applied to fiber products and paper products in the form of organic solvents or aqueous emulsions. The applications include, for example, padding, dipping, spraying, printing, coating, gravure coating and foam laminating. The polymeric resins suitable for use in such treatment of fiber products and paper products include, for example, starch, carboxymethylcellulose, urethane resins, acrylate resins, epoxy resins, vinyl chloride resins, vinyl acetate resins, fluorinated resins, silicone resins, polyamide resins, polyester resins, glyoxal resin, polyvinylidene fluoride resins, styrene resins, butadiene resins, acrylonitrile-butadiene resins, acrylate resins, ethylene-vinyl acetate resins, acrylate-ethylene-vinyl acetate resins and ethylene-vinyl chloride resins.

No particular limitation is placed on the types of the fiber products and paper products which can be treated with the resin compositions of the present invention to impart antibacterial and antifungal processing thereto. They include, for example, various kinds of products formed from synthetic fibers such as polyester fibers, polyamide fibers, acrylic fibers, polyolefin fibers and polyvinyl chloride fibers; semisynthetic fibers such as acetates; regenerated fibers such as rayon; natural fibers such as cotton, flax, wool, silk and pulp; and composite materials obtained from these fibers by mix spinning, mixed weaving, combined twisting, combined weaving, combined knitting or fiber blending. More specifically, they include fibers such as filaments and staple, threads such as filament yarn and spun yarn; textile materials such as woven fabrics, knitted fabrics and nonwoven fabrics; paper-like materials formed of fibers; and fiber products and paper products made of these materials.

The fiber and paper products treated with the resin compositions of the present invention include, for example, linen products for use in hospitals, sanitary products, bedclothes, socks, supporters, carpets, toiletry goods, kitchen utensils, toys, filters for electrical appliances, wet tissue, helmets and wallpaper, etc.

According to a specific embodiment of the present invention, a highly water-absorbing resin may be used as the starting resin. This makes it possible to provide a water-absorbing resin composition which has excellent deodorant properties and can hence be used in sanitary products including, in particular, disposable diapers, and urine disposal articles for pets.

As the highly water-absorbing resin included in this water-absorbing resin composition, there may be used any of the highly water-absorbing resins commonly used in disposable diapers and sanitary products (e.g., sanitary napkins). Examples thereof include starch-based water-absorbing resins such as soluble starch-acrylonitrile graft copolymer and starch-acrylic acid graft copolymer; cellulose-based water-absorbing resins such as crosslinked graft cellulose and crosslinked carboxymethylcellulose; and synthetic polymer-based water-absorbing resins such as partially crosslinked polyoxyethylene, partially crosslinked acrylate or methacrylate polymers, partially crosslinked acrylate or methacrylate copolymers, and vinyl alcohol-acrylate copolymer. It is generally preferable that these resins have the ability to absorb several hundred to several thousand times as much water as their own weight. The resins may be used alone or in combination of two or more.

An antibacterial compound of the above formula (I) may be incorporated in such a highly water-absorbing resin according to any of the per se known methods. This may be done, for example, (1) by allowing a powder of the highly water-absorbing resin to absorb an aqueous solution containing an appropriate amount of the compound of formula (I), followed drying; (2) by adding an appropriate amount of the compound of formula (I), in the form of a powder or a solution, to the highly water-absorbing resin at any stage of the preparation of the resin; or (3) by mixing a powder of the highly water-absorbing resin with an appropriate amount of the compound of formula (I) in powder form. However, the above-described methods (1) and (2) are preferred for the purpose of highly dispersing the compound of formula (I).

The water-absorbing resin composition prepared in the above-described manner may be processed into various forms. No particular limitation is placed on such forms. For example, the water-absorbing resin composition may be formed into powders, granules, sheets or fibers according to the intended use of the final product, and the like. Moreover, it may be formed into water-absorbing fibers of two-layer structure in which an acrylic fiber is incorporated as the core (e.g., "Lanseal F" manufactured by Toyobo Co., Ltd.).

The amount of the antibacterial compound of formula (I) incorporated in the highly water-absorbing resin is not strictly limited, but may vary according to the type of the antibacterial compound used, and the like. However, the antibacterial compound of formula (I) is generally used in an amount of 0.001 to 10 parts by weight, preferably 0.005 to 5 parts by weight, and more preferably 0.01 to 2 parts by weight, per 100 parts by weight of the resin.

When the highly water-absorbing resin having the antibacterial compound of formula (I) incorporated therein as described above is used as a water-absorbing resin for sanitary products and, in particular, disposable diapers, it becomes possible to provide hygienic disposable diapers which can effectively prevent the generation of an offensive odor arising from urinary excretion. Specifically, in disposable diapers consisting of a water-pervious facing sheet, a water-impervious backing sheet, and a water-absorbing layer interposed between these sheets, the highly water-absorbing resin conventionally used in the water-absorbing layer may be replaced by the water-absorbing resin composition of the present invention. The disposable diapers thus obtained can inhibit the growth of bacteria decomposing urea and other compounds present in urine to produce ammonia, methylamine, etc., and thereby prevent the generation of an offensive odor due to the decomposition of urea and other compounds. Moreover, they can also inhibit the growth of various microorganisms such as *Escherichia coli* and *Candida* species, and can hence be expected to improve unhygienic conditions attributable to such various microorganisms.

In addition, when the highly water-absorbing resin having the antibacterial compound of formula (I) is used in urine disposal articles for pets, it can be expected that they have an excellent deodorant effect.

It frequently happens that pets are kept at home. Especially when pets are kept indoors, the keeper is often troubled with the disposal of excretion therefrom and an offensive odor emitted thereby. Litter for a cat box (cat sand) is commonly used as a urine disposal article for pets. Generally, litter comprising ordinary sand is used to absorb and retain excretion from pets. After a while, the litter is washed, dried and reused, but this has the disadvantage of requiring much labor. Moreover, if the interval between replacements is lengthened, an unhygienic condition is developed owing to the emission of an offensive odor and the generation of various microorganisms. In order to solve these problems, litter comprising a highly water-absorbing resin and, moreover, such litter having added thereto antibacterials and a deodorant have recently come into the market. In the present circumstance, however, they are not satisfactorily effective in preventing the generation of an offensive odor. Although some patience or habituation may make the keeper insensitive to the odor of pets because they are practically members of the family, occasional visitors tend to suffer from an unpleasant odor.

As demonstrated in the examples which will be given later, the deodorant water-absorbing resin compositions of the present invention can more effectively prevent the generation of an offensive odor due to the decomposition of urine, and the growth of various microorganisms, than other antibacterials. Accordingly, the deodorant water-absorbing resin compositions of the present invention can contribute greatly to the prevention of an offensive odor arising from pets, the maintenance of a hygienic environment, and a decrease in the freq offensive odor uency of exchange of urine disposal articles for pets.

The present invention is further illustrated by the following examples. However, these examples are not to be construed to limit the scope of the invention.

EXAMPLE 1

Antibacterial urethanes were obtained by adding 1 phr of N,N'-hexamethylenebis(4-carbamoyl-1-decylpyridinium bromide) (hereinafter referred to as "Dimer 38"), 4,4'-(tetramethylenedicar-bonyldiamino)bis(1-decylpyridinium bromide) (hereinafter referred to as "Dimer 136) or inorganic antibacterials containing silver to an ether type urethane and an ester type urethane. The antibacterial urethanes thus obtained were subjected to antibacterial tests according to a film covering method. Concretely, each specimen (5 cm×5 cm) was placed in a sterile petri dish, and the test surface was inoculated with 0.5 ml of a cell suspension and was covered with a sterile polyethylene film. The petri dish was covered and allowed to stand at 37° C. for 24 hours. Thereafter, using SCDLP medium (9.5 ml), the bacterial cells attached to the specimen and the coating film were thoroughly washed out into the another sterile petri dish. The viable cell number present in 1 ml of the washings was counted according to the agar dilution method. Three specimens were tested for each sample, and the viable cell count was calculated as the average of the three specimens. For this purpose, two strains of bacteria, *Staphylococcus aureus* IFO 12732 and *Escherichia coli* K12 W3110, were used. The results thus obtained are shown in Table 1.

TABLE 1

| | Sample | | Viable cell count | |
|---|---|---|---|---|
| | Antibacterials | Concentration | *Staphylococcus aureus* | *Escherichia coli* |
| Ether type urethane | — | — | $1.6 \times 10^8$ | $5.2 \times 10^4$ |
| | Dimer 38 | 1 phr | <200 | <200 |
| | Dimer 136 | | <200 | <200 |
| | Inorganic antibacterials containing silver | | <200 | <200 |
| Ester type urethane | — | — | <200 | $2.8 \times 10^7$ |
| | Dimer 38 | 1 phr | <200 | <200 |
| | Inorganic antibacterials containing silver | | <200 | <200 |
| | Control | | $2.2 \times 10^6$ | $4.0 \times 10^7$ |
| | Initial cell number | | $3.3 \times 10^5$ | $1.2 \times 10^6$ |

It can be seen from the results shown above in Table 1 that the sheets containing Dimer 38 or Dimer 136 have excellent antibacterial efficiency.

EXAMPLE 2

Antifungal vinyl chloride polymer sheets were formed from polyvinyl chloride having 0.5% of Dimer 38, Dimer 136 or inorganic antibacterials containing zinc. Fungus resistance of the antifungal sheets were assessed by the modified method of JIS Z 2911 (Japanese Industrial Standards Committee, 1992). Concretely, a specimen (4 cm×4 cm) of each sheet was placed in a petri dish containing a mineral nutrient agar, and 0.5 ml of the mixed spore suspension was uniformly inoculated on the agar and the specimen. The petri dish was covered, incubated at 28° C. for 9 weeks, and observed for the growth of fungi at intervals of one week. For this purpose, the blend of spore suspension of four strains of fungi, *Aspergillus niger* IFO 6341, *Penicillium funiculosum* IFO 6345, *Chaetomium globosum* IFO 6347 and *Aureobasidium pullulans* IFO 6353, were used. The results thus obtained are shown in Table 2. The symbols (○, Δ and X) given in Table 2 have the following meanings.

○=No growth of fungi was recognized on the sheet inoculated with the blend of spore suspension.

Δ=The growth of fungi was recognized in ⅓ or less of the total area of the sheet inoculated with the blend of spore suspension.

X=The growth of fungi was recognized in more than ⅓ of the total area of the sheet inoculated with the blend of spore suspension.

TABLE 2

| | Fungus resistance | | | |
|---|---|---|---|---|
| Week | Dimer 38 | Dimer 136 | Inorganic antibacterials containing zinc | Control |
| 1 | | | | Δ |
| 2 | | | | X |
| 3 | | | | X |
| 4 | | | Δ | X |
| 5 | X | | X | X |
| 6 | X | | X | X |
| 7 | X | | X | X |
| 8 | X | | X | X |
| 9 | X | | X | X |

It can be seen from the results shown in Table 2 that the sheet with Dimer 38 or Dimer 136 exhibit stronger antifungal efficiency than the commercially available sheet containing inorganic antibacterials containing zinc. Especially in the case of the Dimer 136-containing antifungal sheet, no growth of fungi was observed even after 9 weeks of culturing, indicating that it has excellent antifungal efficiency.

EXAMPLE 3

Water-absorbing resins containing antibacterials (herein referred to as "antibacterial SAPs") were prepared by allowing 1 g of a highly water-absorbing resin powder ("AQUAPEARL ZS45"; manufactured by Mitsubishi Chemical Co., Ltd.) to absorb 10 g of an aqueous solution of antibacterials having each concentration of 500, 110 or 20 ppm, and then drying the resin at 130° C. The antibacterials comprised (Dimer 38), N,N'-hexamethylene-bis(4-carbamoyl-1-decylpyridinium acetate) (hereinafter referred to as Dimer 38A) or benzalkonium chloride. One gram of each of the antibacterial SAPs was placed in a sterile petri dish, inoculated with 10 ml of the cell suspension in stationary phase, and was incubated at 37° C. for 24 hours. Thereafter, 1 g of the resin solution, which was in the form of a gel, was taken and added to 9 ml of sterilized physiological saline, followed by vigorous agitation. Then, the viable cell count present in the supernatant was observed. For this purpose, two strains of bacteria, MRSA (*Staphylococcus aureus* JC1) and *Escherichia coli* K12 W3110, were used. The results thus obtained are shown in Table 3.

TABLE 3

| Sample | | Concentration | Viable cell count | |
|---|---|---|---|---|
| | Antibacterials | (ppm) | MRSA | *Escherichia coli* |
| Antibacterial SAP | Dimer 38 | 500 | 0 | 0 |
| | | 100 | 0 | 0 |
| | | 20 | 0 | 0 |
| | Dimer 38A | 500 | 0 | 0 |
| | | 100 | 0 | 0 |
| | | 20 | 0 | $5.0 \times 10^2$ |
| | benzalkonium chloride | 500 | 0 | 0 |
| | | 100 | 0 | 0 |
| | | 20 | 0 | $3.0 \times 10^6$ |
| Control | | | $3.0 \times 10^6$ | $2.7 \times 10^7$ |
| Initial cell number | | | $8.3 \times 10^5$ | $1.6 \times 10^6$ |

It can be seen from the results shown above in Table 3 that the SAPs containing Dimer 38 or Dimer 38A have excellent antibacterial efficiency.

EXAMPLE 4

Antibacterial SAPs containing Dimer 38, Dimer 38A or benzalkonium chloride were prepared in the same method as in Example 3. One gram of each of the antibacterial SAPs thus obtained was placed in a test tube, to which 10 ml of human urine and 1 ml of the cell suspension (about $10^6$ cells/ml) of *Proteus mirabilis* IFO 3849 were added. The test tube was incubated at 37° C. After 6 and 24 hours, the concentration of ammonia in the test tube was measured with a smell sensor (Portable Smell Sensor XP-329; manufactured by Shin Cosmos Electric Co., Ltd.). The results are shown in Table 4.

TABLE 4

| | Sample | | Ammonia concentration (ppm) | |
|---|---|---|---|---|
| | Antibacterials | Concentration (ppm) | 6 hours | 24 hours |
| Antibacterial SAP | Dimer 38 | 500 | Not detected | Not detected |
| | Dimer 38A | | Not detected | Not detected |
| | benzalkonium chloride | | 27 | 125 |
| | Control | | 687 | 9331 |

It can be seen from the results shown in Table 4 that the SAPs containing Dimer 38 or Dimer 38A caused no ammonia to be detected and hence have excellent deodorant efficiency.

REFERNCE EXAMPLE 1

The minimum inhibitory concentrations (MICs), namely the bacteriostasis powers, of Dimer 38 and Dimer 136 were determined and compared with that of benzalkonium chloride. Their minimum inhibitory concentrations (MICs) of antimicrobials were measured by the broth dilution method. Concretely, using nutrient broth, the cell concentration in stationary phase was adjusted to $10^6$ cells/ml, and aliquots thereof were mixed with serially diluted solutions of each antibacterials. These mixtures were incubated at 37° C. for 24 hours and the MICs were determined by visual inspection. In these tests, 8 strains of gram-negative bacteria and 4 strains of gram-positive bacteria were used. The results are shown in Table 5.

TABLE 5

| | MIC (ppm) | | |
|---|---|---|---|
| Bacteria | Dimer 38 | Dimer 136 | Benzalkonium chloride |
| Pseudomonas aeruginosa ATCC 27583 | 5 | 5 | 25 |
| Pseudomonas aeruginosa ATCC 10145 | 5 | 5 | 25 |
| Klebsiella pneumoniae ATCC 4352 | 2.5 | 2.5 | 5 |
| Klebsiella pneumoniae ATCC 13883 | 5 | 1 | 50 |
| Proteus rettgeri NIH 96 | 5 | 2.5 | 25 |
| Proteus mirabilis IFO 3849 | 25 | 10 | 100 |
| Escherichia coli K12 OUT 8401 | 1 | 1 | 5 |
| Escherichia coli K12 W3110 | 2.5 | 2.5 | 10 |
| Bacillus subtilis ATCC 6633 | 0.5 | 0.5 | 2.5 |
| Bacillus cereus IFO 3001 | 1 | 1 | 2.5 |
| Staphylococcus aureus IFO 12732 | 1 | <0.5 | 2.5 |
| Staphylococcus aureus JC1 (MRSA) | 0.5 | 0.5 | 10 |

It is evident from the results shown in Table 5 that Dimer 38 and Dimer 136 exhibit equally strong bacteriostatic efficiency against all of the 8 strains of gram-negative bacteria including *Escherichia coli* and the 4 strains of gram-positive bacteria including MRSA, and hence have wide bacteriostatic spectra over that of benzalkonium chloride. When attention is paid to the bacteriostasis against *Proteus mirabilis* IFO 3849 that is a bacterium producing an enzyme (urease) capable of degrading urea and other compounds to ammonia, methylamine, etc., the bacteriostasis of Dimer 38 is four times and that of Dimer 136 is ten times stronger, as compared with that of benzalkonium chloride.

REFERENCE EXAMPLE 2

The minimum inhibitory concentrations (MICs), namely the antifungal efficiency, of Dimer 38 and Dimer 136 were determined and compared with that of 2-(4-thiazolyl) benzimidazole (hereinafter referred to as "TBZ"). (MICs) were measured by the broth dilution method. Concretely, using sterilized water containing a humectant, spore suspensions were prepared from preincubated fungi, and aliquots thereof were mixed with serially diluted solutions of each antibacterial or antifungal agent. These mixtures were incubated at 27° C. for 1 week and the MICs were determined by visual inspection. In these antifungal tests, 10 strains of fungi were used. The results thus obtained are shown in Table 6.

TABLE 6

| | MIC (ppm) | | |
|---|---|---|---|
| Fungi | Dimer 38 | Dimer 136 | TBZ |
| Aspergillus niger TSY 0013 | 10 | 10 | 25 |
| Aspergillus niger IFO 6341 | 10 | 10 | 25 |
| Aspergillus terreus IFO 6346 | 2.5 | 10 | 10 |
| Aureobasidium pullulans IFO 6353 | 0.5 | 2.5 | 0.5 |
| Chaetomium globosum IFO 6347 | 1 | 2.5 | 1 |
| Cladosporium cladosporioides IFO 6348 | 2.5 | 2.5 | 1 |
| Gliocladium virens IFO 6355 | 0.5 | 1 | 1 |
| Trichoderma viride IFO 30498 | 5 | 5 | 25 |
| Penicillium funiculosum IFO 6345 | 2.5 | 2.5 | 1 |
| Rhizopus nigricans SN 32 | 10 | 10 | 50 |

It is evident from the results shown in Table 6 that, as compared with TBZ, both of Dimer 38 and Dimer 136 exhibit equal or stronger antifungal efficiency against all of the 10 strains of fungi, and hence have wide antifungal spectra.

As described above, the antibacterial and antifungal resin compositions of the present invention each comprise a polymeric resin containing an antibacterial bis-pyridinium compound which not only inhibits the growth of bacteria and shows a wide antibacterial spectrum than usual Quaternary ammonium salt compounds, but also has an antifungal effect on fungi. Consequently, they can be used in a wide range of applications requiring anti-bacterial and antifungal properties from the viewpoint of health and hygiene, and can be expected to improve unhygienic conditions attributable to bacteria and fungi.

What is claimed is:

1. An antibacterial and antifungal resin composition comprising a polymeric resin and an antibacterial bis-pyridinium compound of the general formula

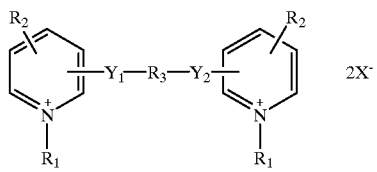

(I)

wherein the two $R_1$ may be the same or different, and each represent an alkyl group of 1 to 18 carbon atoms or an alkenyl group of 3 to 18 carbon atoms; the two $R_2$ may be the same or different, and each represent a hydrogen atom, a halogen atom, a hydroxyl group, an amino group, an alkyl group of 1 to 6 carbon atoms, or an alkoxy group of 1 to 3 carbon atoms; $R_3$ represents an alkylene group of 2 to 18 carbon atoms, an alkenylene group of 3 to 18 carbon atoms, or a phenylene or xylylene group which may optionally be substituted by an alkyl group of 1 to 18 carbon atoms, an alkoxy group of 1 to 6 carbon atoms, or an alkoxycarbonyl group of 2 to 6 carbon atoms; $Y_1$ represents —NHCO—, —CONH—, —NHCS—, —COO—, —COS—, —O— or —S—; $Y_2$ represents —CONH—, —NHCO—, —CSNH—, —OOC—, —SOC—, —O— or —S—; and X represents an anion.

2. A deodorant water-absorbing resin composition comprising a highly water-absorbing resin and an antibacterial bis-pyridinium compound of the general formula (I) as defined in claim 1.

3. The resin composition of claim 1 wherein, in formula (I), the two $R_1$ may be the same or different, and each represent an alkyl group of 8 to 18 carbon atoms; the two $R_2$ may be the same or different, and each represent a hydrogen atom or a chlorine atom; $R_3$ represents an alkylene group of 3 to 8 carbon atoms, a phenylene group or a xylylene group; $Y_1$ represents —NHCO—, —CONH—, —COO— or —S—; $Y_2$ represents —CONH—, —NHCO—, —OOC— or —S—; and X represents a halogen ion or an acetate ion.

4. The resin composition of claim 1 wherein the compound of formula (I) is selected from the group consisting of
N,N'-hexamethylenebis(4-carbamoyl-1-decylpyridinium bromide),
N,N'-hexamethylenebis(4-carbamoyl-1-decylpyridinium acetate),
4,4'-(tetramethylenedicarbonyldiamino)bis(1-decylpyridinium bromide),
4,4'-(tetramethylenedicarbonyldiamino)bis(1-decylpyridinium acetate),
1,4-tetramethylenebis(4-carbamoyl-1-hexadecylpyridinium bromide),
1,6-hexamethylenebis(3-carbamoyl-1-dodecylpyridinium bromide),
1,6-octamethylenebis(3-carbamoyl-1-tetradecylpyridinium bromide),
3,3'-(1,3-trimethylenedicarbonyldiamino)bis(1-dodecylpyridinium bromide),
4,4'-(p-xylyldithio)bis(1-octylpyridinium iodide),
3,3'-(m-xylyldithio)bis(1-tetradecylpyridinium bromide),
N,N'-(p-phenylene)bis(4-carbamoyl-1-octylpyridinium bromide),
N,N'-(m-phenylene)bis(3-carbamoyl-1-dodecylpyridinium bromide),
4,4'-(p-phthalamido)bis(1-octylpyridinium bromide),
3,3'-(m-phthalamido)bis(1-octadecylpyridinium iodide),
4,4'-(1,8-octamethylenedioxy)bis(1-dodecylpyridinium bromide),
3,3'-(1,6-hexamethylenedioxy)bis(1-hexadecylpyridinium bromide),
4,4'-(1,6-hexamethylenedioxydicarbonyl)bis(1-octylpyridinium bromide),
3,3'-(1,6-tetramethylenedioxydicarbonyl)bis(1-dodecylpyridinium bromide),
4,4'-(1,4-tetramethylenedicarbonyldioxy)bis(1-octylpyridinium bromide),
3,3'-(p-phthaloyldioxy)bis(1-decylpyridinium chloride),
4,4'-(1,8-octamethylenedicarbonyldithioxy)bis(1-octadecylpyridinium bromide) and
3,3'-(m-phthaloyldithioxy)bis(1-decylpyridinium iodide).

5. The resin composition of claim 1 or 2 which contains the compound of formula (I) in an amount of 0.001 to 10 parts by weight per 100 parts by weight of the resin.

6. A film, sheet, plate, fiber or other three-dimensional article formed of the resin composition of claim 1.

7. An antibacterial paint containing the resin composition of claim 1 as the vehicle.

8. A fiber product or paper product treated with the resin composition of claim 1.

9. A disposable diaper using the resin composition of claim 2 as a water-absorbing material.

10. A urine disposal article for pets comprising the resin composition of claim 2.

* * * * *